(12) United States Patent
Künzler et al.

(10) Patent No.: US 6,428,839 B1
(45) Date of Patent: Aug. 6, 2002

(54) SURFACE TREATMENT OF MEDICAL DEVICE

(75) Inventors: Jay F. Künzler, Canandaigua; David E. Seelye, North Chili, both of NY (US); Joseph C. Salamone, Boca Raton, FL (US)

(73) Assignee: Bausch & Lomb Incorporated, Rochester, NY (US)

(*) Notice: Subject to any disclaimer, the term of this patent is extended or adjusted under 35 U.S.C. 154(b) by 0 days.

(21) Appl. No.: 09/586,941

(22) Filed: Jun. 2, 2000

(51) Int. Cl.$^7$ .................... A61L 31/10; A61L 27/08; G02C 7/04
(52) U.S. Cl. ............... 427/2.1; 427/2.24; 427/2.12; 427/2.28; 427/430.1; 427/445; 351/160 R; 351/160 H
(58) Field of Search .................. 427/2.1, 2.12, 427/2.24, 2.28, 430.1, 445; 351/160 H, 160 R (56) References Cited

U.S. PATENT DOCUMENTS

| 3,663,288 A | | 5/1972 | Miller ........................... 117/1 |
| 3,916,033 A | * | 10/1975 | Merrill ......................... 427/36 |
| 3,925,178 A | * | 12/1975 | Gesser et al. ................ 204/165 |
| 4,055,378 A | | 10/1977 | Feneberg et al. ............ 351/160 |
| 4,122,942 A | | 10/1978 | Wolfson ..................... 206/5.1 |
| 4,143,949 A | | 3/1979 | Chen ........................... 351/160 |
| 4,168,112 A | | 9/1979 | Ellis et al. .................. 351/160 |
| 4,214,014 A | | 7/1980 | Höfer et al. .................. 427/40 |
| 4,287,175 A | | 9/1981 | Katz ............................. 424/78 |
| 4,312,575 A | | 1/1982 | Peyman et al. ............. 351/160 |
| 4,321,261 A | | 3/1982 | Ellis et al. ................... 424/180 |
| 4,436,730 A | | 3/1984 | Ellis et al. ................... 424/180 |
| 4,632,844 A | | 12/1986 | Yanagihara et al. .......... 427/38 |
| 5,397,848 A | | 3/1995 | Yang et al. .................. 525/477 |
| 5,610,252 A | | 3/1997 | Bambury et al. ............ 526/279 |
| 5,616,757 A | | 4/1997 | Bambury et al. ............ 556/419 |
| 5,700,559 A | | 12/1997 | Sheu et al. ................ 428/319.7 |
| 5,705,583 A | | 1/1998 | Bowers et al. .............. 526/277 |
| 5,708,094 A | | 1/1998 | Lai et al. ..................... 525/296 |
| 5,710,302 A | | 1/1998 | Künzler et al. .............. 556/434 |
| 5,712,327 A | * | 1/1998 | Chang et al. ................ 523/107 |
| 5,714,557 A | | 2/1998 | Künzler et al. .............. 526/279 |
| 5,726,733 A | * | 3/1998 | Lai et al. ..................... 351/160 |
| 5,779,943 A | * | 7/1998 | Enns et al. ................... 264/1.7 |
| 5,789,461 A | * | 8/1998 | Nicolson et al. ............ 523/106 |
| 5,807,636 A | | 9/1998 | Sheu et al. .................. 428/403 |
| 5,908,906 A | | 6/1999 | Künzler et al. .............. 526/279 |

FOREIGN PATENT DOCUMENTS

| EP | 0 963 761 A1 | 12/1999 | ........... A61L/27/00 |
| WO | WO 95/04609 | 2/1995 | ............ B05D/7/24 |

* cited by examiner

Primary Examiner—Robert Dawson
Assistant Examiner—Jeffrey B. Robertson
(74) Attorney, Agent, or Firm—John E. Thomas (57) ABSTRACT

The invention provides a method for improving the wettability of a medical device, comprising the steps of:

(a) providing a medical device formed from a monomer mixture comprising a hydrophilic monomer and a silicone-containing monomer, wherein said medical device has not been subjected to a surface oxidation treatment;

(b) contacting a surface of the medical device with a solution comprising a proton-donating wetting agent, whereby the wetting agent forms a complex with the hydrophilic monomer on the surface of the medical device in the absence of a surface oxidation treatment step and without the addition of a coupling agent.

17 Claims, 2 Drawing Sheets

Figure 1. Dependence of lens diameter and water content on P(AA) concentration for RD677

Figure 2. Dependence of Diameter versus Poly(acrylamide-co-acrylic acid) concentration

SURFACE TREATMENT OF MEDICAL DEVICE

FIELD OF THE INVENTION

The present invention is directed to the surface treatment of medical devices including ophthalmic lenses, stents, implants and catheters. In particular, the present invention is directed to a simple, low cost method of modifying the surface of a medical device to increase its wettability.

BACKGROUND

Medical devices such as ophthalmic lenses made from silicone-containing materials have been investigated for a number of years. Such materials can generally be subdivided into two major classes, namely hydrogels and non-hydrogels. Non-hydrogels do not absorb appreciable amounts of water, whereas hydrogels can absorb and retain water in an equilibrium state. Regardless of their water content, both non-hydrogel and hydrogel silicone medical devices tend to have relatively hydrophobic, non-wettable surfaces that have a high affinity for lipids. This problem is of particular concern with contact lenses.

Those skilled in the art have long recognized the need for modifying the surface of such silicone contact lenses so that they are compatible with the eye. It is known that increased hydrophilicity of the contact lens surface improves the wettability of the contact lenses. This in turn is associated with improved wear comfort of contact lenses. Additionally, the surface of the lens can affect the lens's susceptibility to deposition, particularly the deposition of proteins and lipids from the tear fluid during lens wear. Accumulated deposition can cause eye discomfort or even inflammation. In the case of extended wear lenses (i.e. lenses used without daily removal of the lens before sleep), the surface is especially important, since extended wear lens must be designed for high standards of comfort and biocompatibility over an extended period of time.

Silicone lenses have been subjected to plasma surface treatment to improve their surface properties, e.g., surfaces have been rendered more hydrophilic, deposit resistant, scratch-resistant, or otherwise modified. Examples of previously disclosed plasma surface treatments include subjecting contact lens surfaces to a plasma comprising an inert gas or oxygen (see, for example, U.S. Pat. Nos. 4,055,378; 4,122,942; and 4,214,014); various hydrocarbon monomers (see, for example, U.S. Pat. No. 4,143,949); and combinations of oxidizing agents and hydrocarbons such as water and ethanol (see, for example, WO 95/04609 and U.S. Pat. No. 4,632,844). U.S. Pat. No. 4,312,575 to Peyman et al. discloses a process for providing a barrier coating on a silicone or polyurethane lens by subjecting the lens to an electrical glow discharge (plasma) process conducted by first subjecting the lens to a hydrocarbon atmosphere followed by subjecting the lens to oxygen during flow discharge, thereby increasing the hydrophilicity of the lens surface.

U.S. Pat. Nos. 4,168,112, 4,321,261 and 4,436,730, all issued to Ellis et al., disclose methods for treating a charged contact lens surface with an oppositely charged ionic polymer to form a polyelectrolyte complex on the lens surface that improves wettability.

U.S. Pat. No. 4,287,175 to Katz discloses a method of wetting a contact lens that comprises inserting a water-soluble solid polymer into the cul-de-sac of the eye. The disclosed polymers include cellulose derivatives, acrylates and natural products such as gelatin, pectins and starch derivatives.

U.S. Pat. No. 5,397,848 to Yang et al. discloses a method of incorporating hydrophilic constituents into silicone polymer materials for use in contact and intra-ocular lenses.

U.S. Pat. Nos. 5,700,559 and 5,807,636, both to Sheu et al., discloses hydrophilic articles (for example, contact lenses) comprising a substrate, an ionic polymeric layer on the substrate and a disordered polyelectrolyte coating ionically bonded to the polymeric layer.

U.S. Pat. No. 5,705,583 to Bowers et al. discloses biocompatible polymeric surface coatings. The polymeric surface coatings disclosed include coatings synthesized from monomers bearing a center of positive charge, including cationic and zwitterionic monomers.

European Patent Application EP 0 963 761 A1 discloses biomedical devices with coating that are said to be stable, hydrophilic and antimicrobial, and which are formed using a coupling agent to bond a carboxyl-containing hydrophilic coating to the surface by ester or amide linkages.

Thus, it is desired to provide a silicone hydrogel contact lens with an optically clear, hydrophilic surface film that will not only exhibit improved wettability, but which will generally allow the use of a silicone hydrogel contact lens in the human eye for extended period of time. In the case of a silicone hydrogel lens for extended wear, it would be desirable to provide a contact lens with a surface that is also highly permeable to oxygen and water. Such a surface treated lens would be comfortable to wear in actual use and would allow for the extended wear of the lens without irritation or other adverse effects to the cornea. It would be desirable to manufacture such a surface treated lens without the need for an oxidation step such as plasma treatment or corona discharge treatment.

SUMMARY OF THE INVENTION

The present invention is directed to a method for improving the wettability of a medical device, comprising the steps of:

(a) providing a medical device formed from a monomer mixture comprising a hydrophilic monomer and a silicone-containing monomer, wherein said medical device has not been subjected to a surface oxidation treatment, and (b) contacting a surface of the medical device with a solution including a polymer or copolymer of (meth)acrylic acid, whereby the polymer or copolymers of (meth)acrylic acid forms a complex with the hydrophilic monomer on the contact lens surface without a surface oxidation treatment step and without the addition of a coupling agent.

In a preferred embodiment, the meth(acrylic) acid polymer or copolymer comprises acid content of at least 40 mole percent, more preferably at least about 50 mole percent.

The method of the invention requires neither surface oxidation treatment step nor the addition of a coupling agent. The term "coupling agent" means an entity other than the medical device or the hydrophilic coating material that forms a linkage between the surface of the medical device and the hydrophilic coating material. Examples of linkages provided by coupling agents include ester linkages and amide linkages.

DETAILED DESCRIPTION OF THE INVENTION

Figure 1:
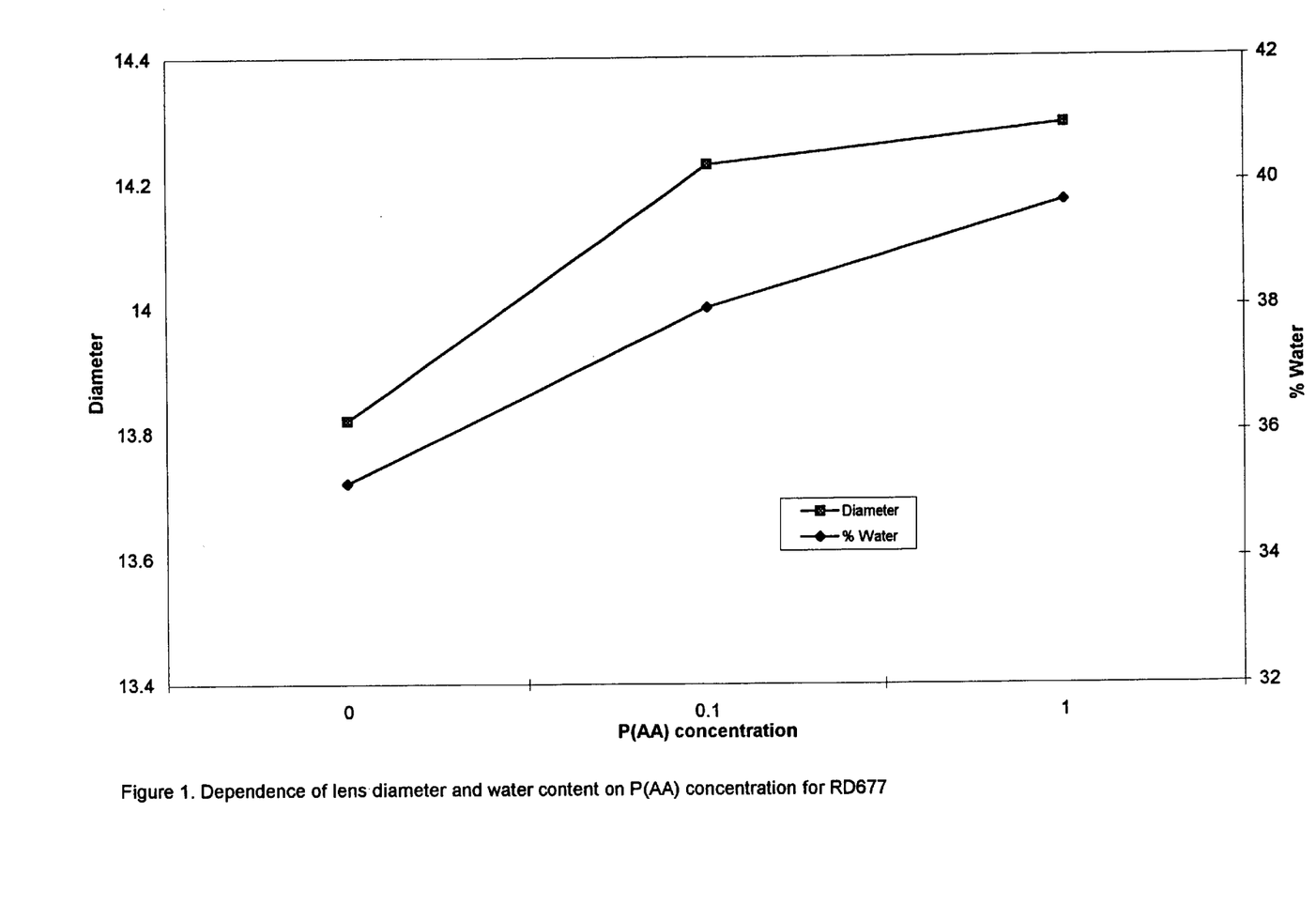
FIG. 1 shows the relationship of lens diameter and water content (weight percent) to poly(acrylic acid) (PAA) concentration for the substrate material identified as RD 677 in Example 1.
Figure 2:
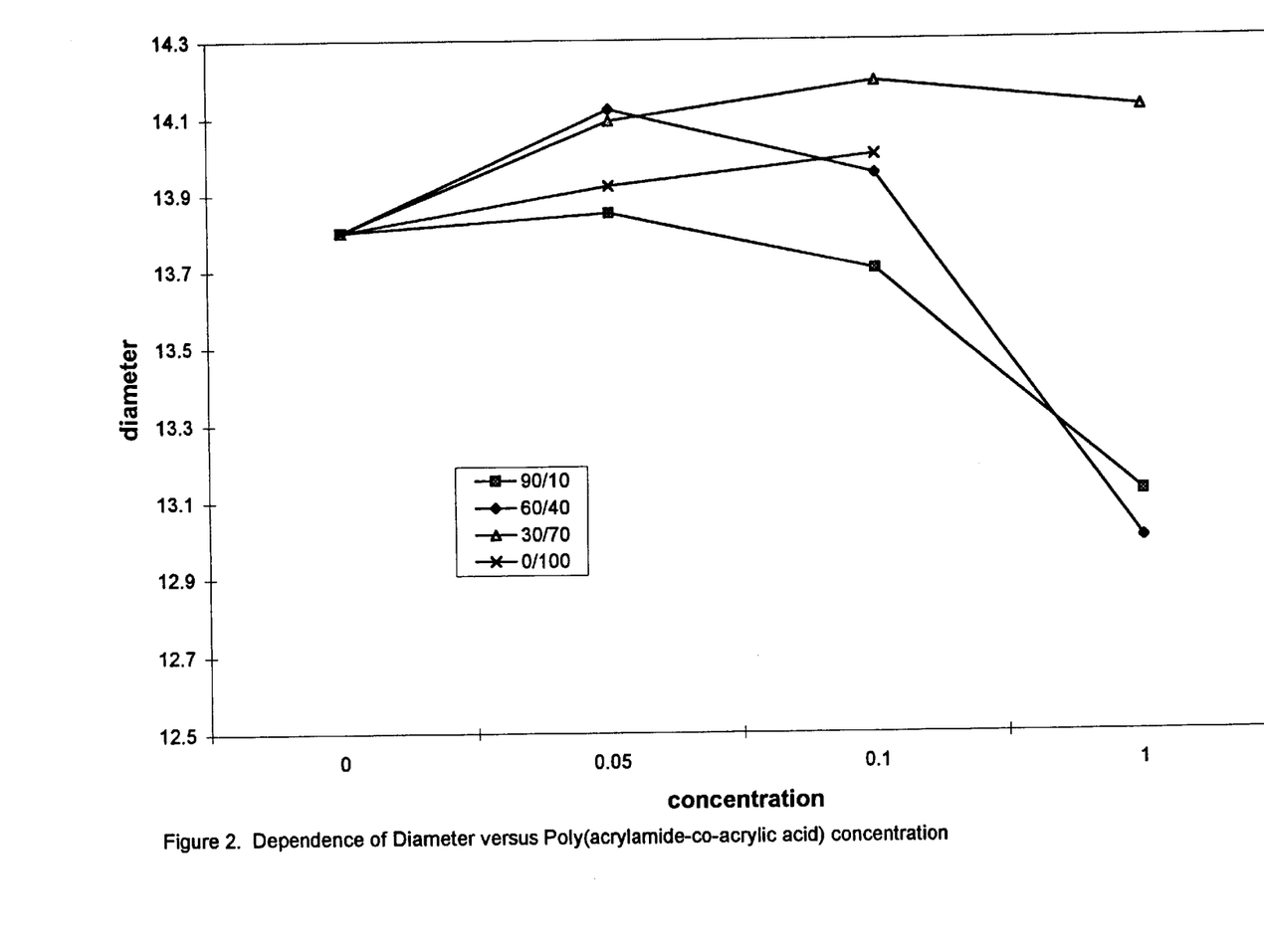
FIG. 2 shows the dependence of lens diameter (y-axis) upon the concentration of poly(acrylamide-co-acrylic acid) for the surface treatment of the substrate material RD1077 in separate experiments using different concentrations of poly (acrylamide-co-acrylic acid) as shown in Table 6.

As mentioned above, the present invention is directed to a silicone hydrogel contact lens having a coating and a method of manufacturing the same, which coating improves the hydrophilicity and lipid resistance of the lens. The poly(acrylic) acid complexation coating allows a lens that could otherwise not be comfortably worn in the eye to be worn in the eye for an extended period of time, for example, more than 24 hours at a time.

The method of the present invention is useful with biocompatible materials including both soft and rigid materials commonly used for opthalmic lenses, including contact lenses. The preferred substrates are hydrogel materials, including silicone hydrogel materials. Particularly preferred materials include vinyl functionalized polydimethylsiloxanes copolymerized with hydrophilic monomers as well as fluorinated methacrylates and methacrylate functionalized fluorinated polyethylene oxides copolymerized with hydrophilic monomers.

Examples of substrate materials useful in the present invention are taught in U.S. Pat. No. 5,908,906 to Kunzler et al.; U.S. Pat. No. 5,714,557 to Kunzler et al.; U.S. Pat. No. 5,710,302 to Kunzler et al.; U.S. Pat. No. 5,708,094 to Lai et al.; U.S. Pat. No. 5,616,757 to Bambury et al.; U.S. Pat. No. 5,610,252 to Bambury et al.; U.S. Pat. No. 5,512,205 to Lai; U.S. Pat. No. 5,449,729 to Lai; U.S. Pat. No. 5,387,662 to Kunzler et al. and U.S. Pat. No. 5,310,779 to Lai; which patents are incorporated by reference as if set forth at length herein.

The invention provides a method for the preparation of wettable silicone-based hydrogel formulations utilizing a poly(acrylic) acid (PAA) surface complexation. Silicone hydrogel formulations containing hydrophilic polymers, such as polydimethylacrylamide or polyvinylpyrrolidinone, are treated with water-based solutions containing PAA or PAA co-polymers to render a lubricious, stable, highly wettable PAA-based surface coating. The treatment is performed at room temperature or under autoclave conditions. No additional oxidative surface treatment such as corona discharge or plasma oxidation is required. No separate coupling agent as described herein is required. The mechanism of this treatment is presently believed to be a surface complexation reaction between PAA and vinylpyrrolidone groups on the lens surface that occurs through a hydrogen bonding mechanism.

Surface coating materials useful in the present invention include P(vinylpyrrolidinone(VP)-co-acrylic acid(AA)), P(methylvinylether-alt-maleic acid), P(acrylic acid-graft-ethyleneoxide), P(acrylic acid-co-methacrylic acid), P(acrylamide-co-AA), P(AA-co-maleic), and P(butadiene-maleic acid).

Coating materials preferred for use in the present invention include those polymers containing carvoxylic acid functionality. Particularly preferred polymers are characterized by acid contents of at least about 30 mole percent, preferably at least about 40 mole percent.

The invention is applicable to a wide variety of materials, and silicone hydrogel contact lens materials are particularly preferred. Hydrogels in general are a well-known class of materials that comprise hydrated, cross-linked polymeric systems containing water in an equilibrium state. Silicone hydrogels generally have a water content greater than about 5 weight percent and more commonly between about 10 to about 80 weight percent. Such materials are usually prepared by polymerizing a mixture containing at least one silicone-containing monomer and at least one hydrophilic monomer. Typically, either the silicone-containing monomer or the hydrophilic monomer functions as a crosslinking agent (a crosslinker being defined as a monomer having multiple polymerizable functionalities) or a separate crosslinker may be employed. Applicable silicone-containing monomeric units for use in the formation of silicone hydrogels are well known in the art and numerous examples are provided in U.S. Pat. Nos. 4,136,250; 4,153,641; 4,740,533; 5,034,461; 5,070,215; 5,260,000; 5,310,779; and 5,358,995.

Examples of applicable silicon-containing monomeric units include bulky polysiloxanylalkyl (meth)acrylic monomers. An example of bulky polysiloxanylalkyl (meth)acrylic monomers are represented by the following Formula I:

(I)

wherein:

X denotes —O— or —NR—;

each $R_1$ independently denotes hydrogen or methyl;

each $R_2$ independently denotes a lower alkyl radical, phenyl radical or a group presented by wherein each $R'_2$, independently denotes a lower alkyl or phenyl radical; and h is 1 to 10.

Some preferred bulky monomers are methacryloxypropyl tris(trimethylsiloxy)silane or tris(trimethylsiloxy) silylpropyl methacrylate, sometimes referred to as TRIS.

Another class of representative silicon-containing monomers includes silicone-containing vinyl carbonate or vinyl carbamate monomers such as: 1,3-bis[4-vinyloxycarbonyloxy)but-1-yl]tetramethyl-disiloxane; 3-(trimethylsilyl)propyl vinyl carbonate; 3-(vinyloxycarbonylthio)propyl-[tris(trimethylsiloxy) silane]; 3-[tris(trimethylsiloxy)silyl]propyl vinyl carbamate; 3-[tris(trimethylsiloxy)silyl]propyl allyl carbamate; 3-[tris (trimethylsiloxy)silyl]propyl vinyl carbonate; t-butyldimethylsiloxyethyl vinyl carbonate; trimethylsilylethyl vinyl carbonate; and trimethylsilylmethyl vinyl carbonate.

An example of silicon-containing vinyl carbonate or vinyl carbamate monomers are represented by Formula II:

$$\left[ \begin{matrix} \phantom{x} \\ \phantom{x} \end{matrix} \underset{R_3}{\overset{}{=}}(CH_2)_q-O-\underset{O}{\overset{\parallel}{C}}-Y' \right]_d R^{Si} \qquad (II)$$

wherein:

Y' denotes —O—, —S— or —NH—;

$R^{Si}$ denotes a silicone-containing organic radical;

$R_3$ denotes hydrogen or methyl:

d is 1, 2, 3 or 4; and q is 0 or 1.

Suitable silicone-containing organic radicals $R^{Si}$ include the following:

—$(CH_2)_n$-Si[$(CH_2)_m$·$CH_3$]$_3$;

—$(CH_2)_n$-Si[OSi$(CH_2)_m$·$CH_3$]$_3$;

$$(CH_2)_{n'}\!-\!\!\left[\begin{matrix} R_5 \\ \mathrm{Si}\!-\!\mathrm{O} \\ R_5 \end{matrix}\right]_{\!e}\!\!-\!R_4$$

$$-(CH_2)_{n'}-\underset{\underset{R_5-Si-R_5}{\overset{O}{\mid}}}{\overset{\overset{R_5-Si-R_5}{\mid}}{Si}}-O-\underset{\underset{R_5}{\mid}}{\overset{\overset{R_5}{\mid}}{Si}}-R_5 \quad \text{and}$$

$$(CH_2)_{n'}\!\!-\!\!\left[\begin{matrix} R_5 \\ \mathrm{Si}\!-\!\mathrm{O} \\ R_5 \end{matrix}\right]_{\!e}\!\!-\!\!\left[\begin{matrix} R_5 \\ \mathrm{Si} \\ R_5 \end{matrix}\right]\!-\!R_5$$

wherein:

$R_4$ denotes

—$(CH_2)_{p'}$—O—C(=O)—CH=CH$_2$ wherein p' is 1 to 6;

$R_5$ denotes an alkyl radical or a fluoroalkyl radical having 1 to 6 carbon atoms;

e is 1 to 200; n' is, 1, 2, 3 or 4; and m' is 0, 1, 2, 3, 4 or 5.

An example of a particular species within Formula II is represented by Formula III.

Another class of silicon-containing monomers includes polyurethane-polysiloxane macromonomers (also sometimes referred to as prepolymers), which may have hard-soft-hard blocks like traditional urethane elastomers. They may be end-capped with a hydrophilic monomer such as HEMA. Examples of such silicone urethanes are disclosed in a variety or publications, including Lai, Yu-Chin, "The Role of Bulky Polysiloxanylalkyl Methacryates in Polyurethane-Polysiloxane Hydrogels," *Journal of Applied Polymer Science,* Vol. 60, 1193–1199 (1996). PCT Published Application No. WO 96/31792 discloses examples of such monomers, which disclosure is hereby incorporated by reference in its entirety. Further examples of silicone urethane monomers are represented by Formulae IV and V:

$$E(*D*A*D*G)_a*D*A*D*E'; \qquad (IV)$$

or $$E(*D*G*D*A)_a*D*G*D*E'; \qquad (V)$$

wherein:

D denotes an alkyl diradical, an alkyl cycloalkyl diradical, a cycloalkyl diradical, an aryl diradical or an alkylaryl diradical having 6 to 30 carbon atoms;

G denotes an alkyl diradical, a cycloalkyl diradical, an alkyl cycloalkyl diradical, an aryl diradical or an alkylaryl diradical having 1 to 40 carbon atoms and which may contain ether, thio or amine linkages in the main chain;

* denotes a urethane or ureido linkage;

a is at least 1;

A denotes a divalent polymeric radical of Formula VI:

$$E-(CH_2)_{m'}-\!\!\left[\begin{matrix} R_s \\ \mathrm{Si}\!-\!\mathrm{O} \\ R_s \end{matrix}\right]_{\!p}\!\!-\!\!\left[\begin{matrix} R_s \\ \mathrm{Si} \\ R_s \end{matrix}\right]\!-(CH_2)_{m'}-E' \qquad (VI)$$

wherein:

each $R_s$ independently denotes an alkyl or fluoro-substituted alkyl group having 1 to 10 carbon atoms which may contain ether linkages between carbon atoms;

m' is at least 1; and p is a number which provides a moiety weight of 400 to 10,000;

each of E and E' independently denotes a polymerizable unsaturated organic radical represented by Formula VII:

$$CH_2=CH-O-C(=O)-O-(CH_2)_4-\underset{\underset{CH_3}{\mid}}{\overset{\overset{CH_3}{\mid}}{Si}}-O-\!\!\left[\begin{matrix} CH_3 \\ \mathrm{Si}-\mathrm{O} \\ CH_3 \end{matrix}\right]_{\!25}\!\!-\underset{\underset{CH_3}{\mid}}{\overset{\overset{CH_3}{\mid}}{Si}}-(CH_2)_4-O-C(=O)-O-CH=CH_2 \qquad (III)$$

(VII)

wherein:

$R_6$ is hydrogen or methyl;

$R_7$ is hydrogen, an alkyl radical having 1 to 6 carbon atoms, or a —CO—Y—$R_9$ radical wherein Y is —O—, —S— or —NH—;

$R_8$ is a divalent alkylene radical having 1 to 10 carbon atoms;

$R_9$ is a alkyl radical having 1 to 12 carbon atoms;

X denotes —CO— or —OCO—;

Z denotes —O— or —NH—;

Ar denotes an aromatic radical having 6 to 30 carbon atoms;

w is 0 to 6; x is 0 or 1; y is 0 or 1; and z is 0 or 1.

A more specific example of a silicone-containing urethane monomer is represented by Formula (VIII):

(VIII)

wherein m is at least 1 and is preferably 3 or 4, a is at least 1 and preferably is 1, p is a number which provides a moiety weight of 400 to 10,000 and is preferably at least 30, $R_{10}$ is a diradical of a diisocyanate after removal of the isocyanate group, such as the diradical of isophorone diisocyanate, and each E" is a group represented by:

A preferred silicone hydrogel material comprises (in the bulk monomer mixture that is copolymerized) 5 to 50 percent, preferably 10 to 25, by weight of one or more silicone macromonomers, 5 to 75 percent, preferably 30 to 60 percent, by weight of one or more polysiloxanylalkyl (meth)acrylic monomers, and 10 to 50 percent, preferably 20 to 40 percent, by weight of a hydrophilic monomer. In general, the silicone macromonomer is a poly (organosiloxane) capped with an unsaturated group at two or more ends of the molecule. In addition to the end groups in the above structural formulas, U.S. Pat. No. 4,153,641 to Deichert et al. discloses additional unsaturated groups, including acryloxy or methacryloxy. Fumarate-containing materials such as those taught in U.S. Pat. Nos. 5,512,205; 5,449,729; and 5,310,779 to Lai are also useful substrates in accordance with the invention. Preferably, the silane macromonomer is a silicon-containing vinyl carbonate or vinyl carbamate or a polyurethane-polysiloxane having one or more hard-soft-hard blocks and end-capped with a hydrophilic monomer.

Suitable hydrophilic monomers include those monomers that, once polymerized, can form a complex with poly (acrylic acid). The suitable monomers form hydrogels useful in the present invention and include, for example, monomers that form complexes with poly(acrylic acid) and its derivatives. Examples of useful monomers include amides such as dimethylacrylamide, dimethylmethacrylamide, cyclic lactams such as n-vinyl-2-pyrrolidone and poly(alkene glycols) functionalized with polymerizable groups. Examples of useful functionalized poly(alkene glycols) include poly (diethylene glycols) of varying chain length containing monomethacrylate or dimethacrylate end caps. In a preferred embodiment, the poly(alkene glycol) polymer contains at least two alkene glycol monomeric units. Still further examples are the hydrophilic vinyl carbonate or vinyl carbamate monomers disclosed in U.S. Pat. No. 5,070,215, and the hydrophilic oxazolone monomers disclosed in U.S. Pat. No. 4,910,277. Other suitable hydrophilic monomers will be apparent to one skilled in the art.

In particular regard to contact lenses, the fluorination of certain monomers used in the formation of silicone hydrogels has been indicated to reduce the accumulation of deposits on contact lenses made therefrom, as described in U.S. Pat. Nos. 4,954,587, 5,079,319 and 5,010,141. Moreover, the use of silicone-containing monomers having certain fluorinated side groups, i.e. —(CF$_2$)—H, have been found to improve compatibility between the hydrophilic and silicone-containing monomeric units, as described in U.S. Pat. Nos. 5,387,662 and 5,321,108.

Solvents useful in the surface treatment (contacting) step of the present invention include solvents that readily solubilize proton donating solutes such as carboxylic acids, sulfonic acids, fumaric acid, maleic acids, anhydrides such as maleic anhydride and functionalized alcohols such as vinyl alcohol. Preferred solvents include tetrahydrofuran (THF), acetonitrile, N,N-dimethyl formamide (DMF), and water. The most preferred solvent is water.

The surface treatment solution is preferably acidified before the contact step. The pH of the solution is suitably less than 7, preferably less than 5 and more preferably less than 4. In a particularly preferred embodiment, the pH of the solution is about 3.5. For a discussion of the theory underlying the role of pH in complexation reactions in general, see *Advances in Polymer Science,* published by Springer-Verlag, Editor H. J. Cantow, et al, V45, 1982, pages 17–63.

EXAMPLES

Several silicone hydrogel lens formulations were treated, in separate experiments, with a 0.1% PAA, 1.0% PAA and a 0.25% Carbopol solutions. Carbopol is a lightly cross-linked poly(acrylic acid) ("PAA"). The reported molecular weights of the PAA and Carbopol are 450,000 and 2,500,000, respectively.

The samples designated below as RD677 and RD 1077 are vynagels. U.S. Pat. No. 5,616,757 to Bambury et al. teaches methods for making vynagel contact lens materials. The samples designated below as RD954 are fluorogels. U.S. Pat. No. 5,710,302 to Kunzler et al. teaches methods for making fluorogel contact lens materials. The samples designated below as RD933 are fumarates. U.S. Pat. Nos. 5,496,871, 5,449,729, and 5,420,324 teach methods for making fumarate contact lens materials.

Example 1

The surface treatment consists of immersing the lenses in the PAA solution followed by a 30-minute autoclave cycle. The complexation surface treatment of the invention is also effective at room temperature. The lenses are then rinsed in distilled water and re-autoclaved in a suitable buffer, for example a borate buffer.

Excellent wetting characteristics were achieved for this procedure (Table 1). A significant reduction in sessile drop contact angle was observed for both the RD954 (fluorogel) and the RD677 (vynagel) lenses. Inspection of lenses using a cosmetic comparator (Bendix 10×cosmetic comparator Model 10) gives a clarity of 2 for the 1% and 0.1% PAA treated Vynagel lenses and a clarity of 4 for the 0.25% treated Carbopol lenses. The clarity scale for the cosmetic comparator used in the present example is 0 for opaque to 5 for optimum clarity. A value of 2 is an acceptable rating for contact lens applications. Minimal change in water content, lens diameter and mechanical properties were observed following the PAA or Carbopol treatment. Table 1 presents these results, opaque to 5 for optimum clarity. A value of 2 is an acceptable rating for contact lens applications. Minimal change in water content, lens diameter and mechanical properties were observed following the PAA or Carbopol treatment. Table 1 presents these results.

TABLE 1

Mechanical and Physical Property Results For PAA and Carbopol Treated Vynagel and Fluorogel Lenses

| Material | Treatment | Modulus | Diameter | Clarity | % Water | Contact Angle before | Contact Angle after | Lipid deposition (ug) | Protein deposition (ug) |
|---|---|---|---|---|---|---|---|---|---|
| RD677 (vynagel) | test 0.25% carbopol | 115 | 14.274 | 4 | 38.7 | 110 | 65 | | |
| | test 0.1% PAA | 115 | 14.229 | 2 | 38 | 110 | 67 | | |
| | test 1.0% PAA | 150 | 14.293 | 2/3 | 39.7 | 110 | 50 | 51 | 26.7 |
| | control RD677 | 110 | 13.969 | 4 | 35.2 | 110 | | 402 | 0 |
| RD954 (fluorogel) | 1.0% celanex cast | | | | | 105 | 42 | | |
| | 1.0% polypropylene cast | | | | | 101 | 57 | | |
| RD1077 (vynagel) | Control | 99 | 13.82 | | 38.7 | | | | |
| (low acid-no plasma) | 0.1% P(AA) 450K | 93 | | | 41.8 | | | | |
| | 0.05% | | 14 | | na | | | | |

| PAA Conc. | Diameter | % Water |
|---|---|---|
| 0 | 13.82 | 35.2 |
| 0.1 | 14.229 | 38 |
| 1 | 14.293 | 39.7 |

Example 2

Stability of Surface Treatment

A stability study comparing PAA treated lenses was completed. Results are shown in Table 3. RD677 and RD 954 lenses were placed in an 85° C. oven for 7 days (to simulate a one-year shelf life) and 17 days (to simulate a three-year shelf-life). The lenses were then removed from the oven and measured for water and isopropanol content. Test and control lenses gave identical results for percentage water loss and percentage weight loss following the 7- and 17-day test period. The combined data showed that the surface complexation had little effect on the overall stability of the lenses. The IPA follow-up extraction measured water insoluble degradation-by-products. The results of Example 2 are shown below in Table 2.

TABLE 2

| PAA stability Autoclave Treatment Material | Control/Test [PAA] | Baseline % water | % IPA loss | 7 day 85 C. % water | 7 day 85 C. % IPA | 17 day 85 C. % water | 17 day 85 C. % IPA | Baseline mod. | 7 day 85 C. mod. | 17 day 85 C. mod. |
|---|---|---|---|---|---|---|---|---|---|---|
| RD933 | Control | 33.7 | 2.8 | 37.1 | 2.4 | 35.6 | 2.2 | | | |
|  | 0.10% | 36.6 | 2.1 | 37.8 | 1.8 | 36.3 | 2.3 | | | |
| Fluorogel 40 (RD954) | control | 48.1 | 4.9 | 52.1 | 4.6 | 49.2 | 4.5 | | | |
|  | 0.10% | 48.8 | 3.2 | 50.7 | 3 | 48.3 | 8 | | | |
| Vynagel (RD677) | control | 36.9 | 4.6 | 40.5 | 2.7 | 39 |  | | | |
|  | 0.10% | 35.4 | 2.4 | 39.5 | 2.1 | 38.2 | 3 | | | |
|  |  | 40.3 | 1.7 | 39.7 | 2.6 | 38 | 2.3 | | | |
| D5-1077-1185 | 0.1 | 41.8 | 0.5 | 42.5 | 2.2 | 42.2 | 1.5 | 93 | 139 | 147 |
| low acid no plasma | control | 38.7 | 0.7 | 39.8 | 2.1 | 39.8 | 1.5 | 99 | 117 | 129 |

Examples 3 and 4

Tables 3 and 4 provide a list of acid containing polymers that were used in the complexation of RD677 (vynagel). This summary provides data for both the autoclave treatment and a sonication treatment. For the sonication step, the lenses are placed in a beaker containing the polymer solution and sonicated for two hours at a temperature between room temperature and about 40° C. using a Branson Model 5200 sonicator.

Tables 3 and 4 also list the wetting and lubricity characteristics of the treated lenses. The sonication method consists of immersing the lenses in the polymer solution and sonicating the lenses at room temperature for two hours. This procedure offers the advantage that lenses can be surface treated at the lens processing step (following extraction and prior to cosmetic inspection). In the autoclave procedure, the vials need to be re-opened, re-extracted in distilled water and re-autoclaved in borate prior to use.

TABLE 3

Complexation

Complexation via autoclave treatment

| Lens Material | Polymer (0.1% solution unless noted) | Conditions | Surface characteristics | Diameter |
|---|---|---|---|---|
| RD677 test lens | PVP-co-AA (25%) 96K (0.05%) | auto | fair wetting/no lubricity | 14.241 |
|  | PVP-co-AA (25%) 96K (0.1%) | auto | fair wetting/no lubricity | 14.213 |
|  | MVE-alt-MA 1.98M (0.05%) | auto | fair wetting/no lubricity | 14.183 |
|  | MVE-alt-MA 1.98M (0.1%) | auto | fair wetting/no lubricity | 14.145 |
|  | PAA-sodium-graft PEO acidified to 3 (0.05%) | auto | fair wetting/marginal lub | 14.209 |
|  | PAA-sodium-graft PEO acidified to 3 (0.1%) | auto | fair wetting/marginal lubricity | 14.145 |
|  | P(acrylamide-co-acrylic acid) 200K acidified 30/70 (0.05) | auto | excellent wetting/lubricity | 14.308 |
|  | P(acrylamide-co-acrylic acid) 200K acidified 30/70 (0.1) | auto | excellent wetting/lubricity | na |
|  | Carbopol 940 (0.05%) | auto | excellent wetting/lubricity | na |
|  | Carpopol 940 (0.1%) | auto | good wetting/fair lubricity | 14.166 |
| RD677 control lens | borate buffer | auto | no wetting or lubricity | 14.195 |

TABLE 4

Complexation

| Lens Material | Polymer (0.1% solution unless noted) | Conditions | Surface characteristics | Diameter |
|---|---|---|---|---|
| RD677 test lens | P(vinylpyrolidinone(VP)-co-acrylic acid(AA)) (25% AA) 96K | balsonic 2 hrs | good wetting/lubricious | 14.213 |
|  | P(methylvinylether-alt-maleic acid) 1.98M | balsonic 2 hrs | good wetting/fair lubricity | 14.183 |
|  | P(acrylic acid-graft-ethyleneoxide) | balsonic 2 hrs | good wetting/fair lubricity | 14.145 |
|  | P(acrylic acid-co-methacrylic acid 34K | balsonic 2 hrs | fair wetting/fair lubricity | |
|  | P(acrylamide-co-AA) Mw 200K 10% AA | balsonic 2 hrs | poor wetting/no lubricity | |
|  | P(acrylamide-co-AA Mw 200K 1.5% AA | balsonic 2 hrs | pQor wetting/no lubricity | |
|  | P(AA) 4M | balsonic 2 hrs | good wetting/lubricious | |
|  | P(AA-co-maleic) to ph3 70K | balsonic 2 hrs | excellent wetting and lubricity | |
|  | P(AA) followed by PVP 1% Mw 1.3M | balsonic 2 hrs | no wetting/no lubricity | |
|  | P(AA) followed by imidazolidinone 1% solution | balsonic 2 hrs | no wetting/no lubricity | |
|  | P(maleic acid) polyscience | balsonic 2 hrs | poor wetting/no lubricity | |
|  | P(butadiene-maleic acid (polyscience) | balsonic 2 hrs | good wetting/fair lubricity | |
|  | P(acrylamide-co-acrylic acid 200K acidified 30/70 | balsonic 2 hrs | excellent wetting and lubricity | |
|  | 1% pvp | balsonic 2 hrs | no wetting/no lubricity | |

TABLE 4-continued

| | Complexation | | | |
|---|---|---|---|---|
| Lens Material | Polymer (0.1% solution unless noted) | Conditions | Surface characteristics | Diameter |
| | 940 (0.1%) | balsonic 2 hrs | good wetting/lubricity | 14.166 |
| RD677 control lens | borate buffer | balsonic 2 hrs | no wetting/no lubricity | 14 |

Tables 5 and 6 show the sonication and autoclave treatment results for material RD1077. Similar wetting and lubricity characteristics were achieved. FIG. 3 shows the dependence of lens diameter versus concentration of the poly(acrylamide-co-acrylic acid) solution.

TABLE 5

| | Complexation | | | | |
|---|---|---|---|---|---|
| Lens Material | Polymer and concentration | Conditions | Surface characteristics (11/06/98) | Diameter | Clarity |
| RD1077 test lens | PVP-co-AA (25%) 96K (1.0) | autoclave | light haze, excellent wetting, lubricity | 14.196 | 2 |
| | 0.1 | autoclave | clear, poor wetting | 14.06 | 4 |
| | 0.05 | autoclave | good clarity, lubricity and wetting | 13.92 | |
| | MVE-alt-MA 1.98M (1.0) | autoclave | slight haze, excellent wetting, lubricity | 14.14 | |
| | 0.1 | autoclave | slight haze, excellent wetting | 14.03 | |
| | 0.05 | autoclave | slight haze, excellent wetting, lubricity | 13.95 | |
| | PAA-sodium-graft PEO acidified to 3 (0.1) | autoclave | good clarity, no wetting, no lubricity | na | |
| | | autoclave | na | na | |
| | P(acrylamide-co-acrylic acid) 200K acidified 90/10 (1.0) | autoclave | clear, good wetting, no lubricity | 13.12 | |
| | 0.1 | autoclave | poor wetting, no lubricity | 13.7 | |
| | 0.05 | autoclave | poor wetting, no lubricity | 13.85 | |
| | P(acrylamide-co-acrylic acid) 200K acidified 60/40 (1.0) | autoclave | clear, excellent wetting, fragile | 13 | 2 |
| | 0.1 | autoclave | clear, excellent wetting, fragile | 13.98 | 2 |
| | 0.05 | autoclave | slight haze, wets well, lubricious | 14.12 | 2 |
| | P(acrylamide-co-acrylic acid) 200K acidified 30/70 (1.0) | autoclave | clear, good wetting, lubricious | 14.12 | 4 |
| | 0.1 | autoclave | clear, good wetting, lubricious | 14.19 | 4 |
| | 0.05 | autoclave | clear, good wetting, lubricious | 14.09 | 4 |
| | Carpopol 940 (0.1%) | autoclave | light haze, excellent wetting, lubricious | 13.92 | 2 |
| | 0.05 | autoclave | very good wetting, marginal lubricity | 14.01 | 4 |
| | P(AA) 4M (0.1) | autoclave | light haze, good wetting, lubricious | 13.98 | 1 |
| | 0.05 | autoclave | good wetting, marginal lubricity | 13.92 | 3 |
| RD1077 control lens | borate buffer | autoclave | no wetting or lubricity | 13.8 | |

TABLE 6

| | Complexation | | | | |
|---|---|---|---|---|---|
| Lens Material RD1077 | Polymer and concentration | Conditions | Surface characteristics | Clarity | Diameter |
| no plasma | PVP-co-AA (25%) 96K (1.0) | 2 hr sonication | light haze, excellent wetting and lubricity | 3 | 14.14 |
| | 0.1 | 2 hr sonication | clear, poor wetting | 5 | 14.03 |
| | 0.05 | 2 hr sonication | good clarity, marginal lubricity and wetting | | 14.02 |
| | MVA-alt-MA 1.98M (1.0) | 2 hr sonication | light haze, excellent wetting and lubricity | 3 | 13.786 |
| | 0.1 | 2 hr sonication | light haze, excellent wetting and lubricity | | 14.065 |
| | 0.05 | 2 hr sonication | light haze, excellent wetting and lubricity | | 14.084 |
| | PAA-sodium-graft PEO acidified to 3 (0.1) | 2 hr sonication | good clarity, no wetting, no lubricity | | na |
| | | 2 hr sonication | na | | na |
| | polyacrylamide-co-acrylic acid 200K acidified 90/10 (1.0) | 2 hr sonication | clear, good wetting, no lubricity | | 13 |
| | 0.1 | 2 hr sonication | poor wetting, no lubricity | | 13.14 |
| | 0.05 | 2 hr sonication | poor wetting, no lubricity | | 13.85 |
| | polyacrylamide-co-acrylic acid 200K acidified 60/40 (1.0) | 2 hr sonication | clear, excellent wetting, fragile | 3 | prec. |
| | 0.1 | 2 hr sonication | clear, excellent wetting, fragile | 3 | na |
| | 0.05 | 2 hr sonication | light haze, excellent wetting and lubricity | | 13.73 |

TABLE 6-continued

| Lens Material RD1077 | Polymer and concentration | Complexation Conditions | Surface characteristics | Clarity | Diameter |
|---|---|---|---|---|---|
| | polyacrylamide-co-acrylic acid 200K acidified 30/70 (1.0) | 2 hr sonication | clear, good wetting, lubricious | 4 | 14.15 |
| | 0.1 | 2 hr sonication | clear, good wetting, lubricious | 3 | 14.075 |
| | 0.05 | 2 hr sonication | clear, good wetting, lubricious | 2 | na |
| | 940 (0.1%) | 2 hr sonication | light haze, excellent wetting, lubricity | 4 | 14.18 |
| | 0.05 | 2 hr sonication | very good wetting, marginal lubricity | 4 | 13.6 |
| | P(AA) 4M (0.1%) | 2 hr sonication | light haze, good wetting, lubricious | 4 | 14.06 |
| | 0.05 | 2 hr sonication | good wetting, marginal lubricity | 4 | 14.05 |
| RD1077 control lens | borate buffer | 2 hr sonication | no wetting or lubricity | 4 | 13.8 | note: wett = wetting and lub = lubricious

Many other modifications and variations of the present invention are possible in light of the teachings herein. It is therefore understood that, within the scope of the claims, the present invention can be practiced other than as herein specifically described.

What is claimed is:

1. A method for improving the wettability of a medical device, comprising the steps of:
   (a) providing a medical device formed from a monomer mixture comprising a hydrophilic monomer and a silicone-containing monomer, wherein said medical device has not been subjected to a surface oxidation treatment;
   (b) contacting a surface of the medical device with a wetting agent solution comprising at least one proton-donating wetting agent selected from the group consisting of P(vinylpyrolidinone(VP)-co-acrylic acid (AA)), P(methylvinylether-alt-maleic acid), P(acrylic acid-graft-ethyleneoxide), P(acrylic acid-co-methacrylic acid), P(acrylamide-co-AA), P(acrylamide-co-AA), P(AA-co-maleic), and P(butadiene-maleic acid), whereby the wetting agent forms a complex with the hydrophilic monomer on the surface of the medical device in the absence of a surface oxidation treatment step and without the addition of a coupling agent.

2. The method of claim 1 wherein said wetting agent solution comprises at least one polymer containing carboxylic acid functionality.

3. The method of claim 1, wherein the medical device comprises in bulk formula 5 to 50 percent by weight of one or more silicone macromonomers and 5 to 50 percent by weight of a hydrophilic monomer.

4. The method of claim 3, wherein the hydrophilic monomer is selected from the group consisting of unsaturated carboxylic acids, vinyl lactams, acrylamides, vinyl carbonate or vinyl carbamate, oxazolone monomers, and mixtures thereof.

5. The method of claim 3, wherein the hydrophilic monomer is selected from the group consisting of methacrylic and acrylic acids, 2-hydroxyethylmethacrylate, N-vinylpyrrolidone, methacrylamide, N,N-dimethylacrylamide, and mixtures thereof.

6. A method for improving the wettability of a medical device, comprising the steps of:
   (a) providing a medical device formed from a monomer mixture comprising a hydrophilic monomer and a silicone-containing monomer, wherein said medical device has not been subjected to a surface oxidation treatment;
   (b) contacting a surface of the medical device with a solution comprising a wetting agent selected from the group consisting of polymers or copolymers of (meth)acrylic acid, whereby the wetting agent forms a complex with the hydrophilic monomer on the surface of the medical device in the absence of a surface oxidation treatment step and without the addition of a coupling agent.

7. The method of claim 6, wherein the medical device comprises in bulk formula 5 to 50 percent by weight of one or more silicone macromonomers and 5 to 50 percent by weight of a hydrophilic monomer.

8. The method of claim 6, wherein the hydrophilic monomer is selected from the group consisting of unsaturated carboxylic acids, vinyl lactams, acrylamides, vinyl carbonate or vinyl carbamate, oxazolone monomers, and mixtures thereof.

9. The method of claim 8, wherein the hydrophilic monomer is selected from the group consisting of methacrylic and acrylic acids, 2-hydroxyethylmethacrylate, N-vinylpyrrolidone, methacrylamide, N,N-dimethylacrylamide, and mixtures thereof.

10. The method of claim 6 wherein said polymer or copolymer of (meth)acrylic acid is characterized by acid content of at least about 40 mole percent.

11. The method of claim 10 wherein said polymer is characterized by acid content of at least about 50 mole percent.

12. The method of claim 1 wherein said medical device is an opthalmic lens.

13. The method of claim 12 wherein said opthalmic lens is a contact lens.

14. The method of claim 13 wherein said contact lens is a silicone hydrogel lens.

15. The method of claim 12 wherein said contact lens is a rigid-gas-permeable lens.

16. A method for improving the wettability of a medical device comprising the steps of:
   (a) providing a medical device formed from a monomer mixture comprising a silicone-containing monomer and at least one hydrophilic monomer selected from the group consisting of N-vinyl-2-pyrrolidone and N,N-dimethylacrylamide, wherein said medical device has not, been subjected to a surface oxidation treatment; and
   (b) contacting a surface of the medical device with a solution comprising at least one selected from the group consisting of poly(acrylic acid) and poly(acrylic acid-co-acrylamide).

17. The method of claim 16 further comprising acidifying said solution of step (b) to provide a solution pH of less than 5.

* * * * *

/

(12) EX PARTE REEXAMINATION CERTIFICATE (8965th)
United States Patent
Künzler et al.

(10) Number: US 6,428,839 C1
(45) Certificate Issued: Apr. 17, 2012

(54) SURFACE TREATMENT OF MEDICAL DEVICE

(75) Inventors: Jay F. Künzler, Canandaigua, NY (US); David E. Seelye, North Chili, NY (US); Joseph C. Salamone, Boca Raton, FL (US)

(73) Assignee: Credit Suisse, New York, NY (US)

Reexamination Request:
No. 90/009,530, Jul. 14, 2009

Reexamination Certificate for:
Patent No.: 6,428,839
Issued: Aug. 6, 2002
Appl. No.: 09/586,941
Filed: Jun. 2, 2000

(51) Int. Cl.
*A61L 29/08* (2006.01)
*A61L 27/00* (2006.01)
*A61L 27/34* (2006.01)
*A61L 29/00* (2006.01)
*A61L 31/10* (2006.01)
*A61L 31/08* (2006.01)
*C08J 7/00* (2006.01)
*C08J 7/04* (2006.01)

(52) U.S. Cl. ............. 427/2.1; 351/160 H; 351/160 R; 427/2.12; 427/2.24; 427/2.28; 427/430.1; 427/445

(58) Field of Classification Search ............ 427/2
See application file for complete search history.

(56) References Cited

To view the complete listing of prior art documents cited during the proceeding for Reexamination Control Number 90/009,530, please refer to the USPTO's public Patent Application Information Retrieval (PAIR) system under the Display References tab.

*Primary Examiner* — E. Leigh McKane (57) ABSTRACT

The invention provides a method for improving the wettability of a medical device, comprising the steps of:
(a) providing a medical device formed from a monomer mixture comprising a hydrophilic monomer and a silicone-containing monomer, wherein said medical device has not been subjected to a surface oxidation treatment;
(b) contacting a surface of the medical device with a solution comprising a proton-donating wetting agent, whereby the wetting agent forms a complex with the hydrophilic monomer on the surface of the medical device in the absence of a surface oxidation treatment step and without the addition of a coupling agent.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1-17 are cancelled.

* * * * *